United States Patent
Soluch et al.

(10) Patent No.: US 11,033,224 B2
(45) Date of Patent: Jun. 15, 2021

(54) SYSTEM AND METHOD FOR MEASURING LIFE PARAMETERS DURING SLEEP

(71) Applicant: NEURO DEVICE GROUP SPOLKA AKCYJNA, Warsaw (PL)

(72) Inventors: Pawel Soluch, Warsaw (PL); Mateusz Orzechowski, Warsaw (PL); Dominika Rogala, Gdansk (PL); Krzysztof Wrotkowski, Lublin (PL); Przemyslaw Tamon, Warsaw (PL); Michal Ksiezopolski, Cisie (PL); Mariusz Giergielewicz, Warsaw (PL)

(73) Assignee: NEURO DEVICE GROUP SPOLKA AKCYJNA, Warsaw (PL)

( * ) Notice: Subject to any disclaimer, the term of this patent is extended or adjusted under 35 U.S.C. 154(b) by 341 days.

(21) Appl. No.: 16/307,573

(22) PCT Filed: Jun. 7, 2016

(86) PCT No.: PCT/EP2016/062924
§ 371 (c)(1),
(2) Date: Dec. 6, 2018

(87) PCT Pub. No.: WO2017/211396
PCT Pub. Date: Dec. 14, 2017

(65) Prior Publication Data
US 2019/0261919 A1    Aug. 29, 2019

(30) Foreign Application Priority Data
Jun. 6, 2016 (PL) .......................... 417418

(51) Int. Cl.
*A61B 5/00* (2006.01)
*A61B 5/08* (2006.01)
*A61B 5/113* (2006.01)

(52) U.S. Cl.
CPC .......... *A61B 5/4818* (2013.01); *A61B 5/0816* (2013.01); *A61B 5/0826* (2013.01);
(Continued)

(58) Field of Classification Search
CPC ... A61B 5/4818; A61B 5/0816; A61B 5/0826; A61B 5/113; A61B 5/7207; A61B 5/746;
(Continued)

(56) References Cited

U.S. PATENT DOCUMENTS 6,062,216 A    5/2000  Corn
2003/0055348 A1    3/2003  Chazal et al.
(Continued)

FOREIGN PATENT DOCUMENTS

GB    2290202 A    * 12/1995 ......... H04L 27/1525
KR    20030066322 A    * 8/2003 ........... A61B 5/1135
(Continued)

OTHER PUBLICATIONS

J. Jin and E. Sánchez-Sinencio, "A Home Sleep Apnea Screening Device With Time-Domain Signal Processing and Autonomous Scoring Capability," in IEEE Transactions on Biomedical Circuits and Systems, vol. 9, No. 1, pp. 96-104, Feb. 2015, doi: 10.1109/TBCAS.2014.2314301. (Year: 2015).*

(Continued)

*Primary Examiner* — Catherine B Kuhlman
*Assistant Examiner* — William A Anderson
(74) *Attorney, Agent, or Firm* — Buchanan Ingersoll & Rooney PC

(57) ABSTRACT

A method for measuring life parameters during sleep by a device including an accelerometer attached to the body of a sleeping subject. The method includes: (a) setting a hysteresis width having a maximum hysteresis value and a minimum hysteresis value; (b) reading, from the accelerometer, values of acceleration in three axes; (c) filtering the values (Continued)

of acceleration in each of the three axes with a band-pass filter to obtain filtered acceleration signals; (d) combining the filtered acceleration signals to obtain a signal level; (e) checking whether the signal level is higher than the current maximum hysteresis value and if so, setting the maximum hysteresis value to the signal level and setting the minimum hysteresis value to the maximum hysteresis value decreased by the hysteresis width; and (f) signaling a breath detection when detecting a transition from a falling edge to a raising edge.

15 Claims, 5 Drawing Sheets

(52) U.S. Cl.
CPC .............. *A61B 5/113* (2013.01); *A61B 5/7207* (2013.01); *A61B 5/746* (2013.01); *A61B 2562/0219* (2013.01)

(58) Field of Classification Search
CPC .......... A61B 2562/0219; A61B 5/4809; A61B 2019/5248; A61B 5/4806–4818; A61B 5/08; G10H 2220/401; A61M 2021/00
See application file for complete search history.

(56) References Cited

U.S. PATENT DOCUMENTS

| 2005/0119586 | A1 | 6/2005 | Coyle et al. |
| 2013/0331723 | A1 | 12/2013 | Hernandez-Silveira et al. |
| 2013/0345585 | A1* | 12/2013 | Gopal Samy ............ A61B 5/08 600/529 |
| 2014/0228692 | A1* | 8/2014 | Chan .................... A61B 5/0472 600/484 |

FOREIGN PATENT DOCUMENTS

| WO | WO-2007143535 A2 * | 12/2007 | ............. G16H 40/63 |
| WO | WO-2013158331 A1 * | 10/2013 | ........... A61B 5/0816 |

OTHER PUBLICATIONS

Machine translation of Patent No. KR 20030066322 A, retrieved from worldwide.espacenet.com, on Dec. 30, 2020 (Year: 2003).*
International Search Report (PCT/ISA/210) dated Aug. 16, 2016, by the European Patent Office as the International Searching Authority for International Application No. PCT/EP2016/062924.
Written Opinion (PCT/ISA/237) dated Aug. 16, 2016, by the European Patent Office as the International Searching Authority for International Application No. PCT/EP2016/062924.
Jin Jiayi, et al., "A Home Sleep Apnea Screening Device With Time-Domain Signal Processing and Autonomous Scoring Capability", IEEE Transactions on Biomedical Circuits and Systems, IEEE, vol. 9, No. 1, pp. 96-104, Feb. 1, 2015, XP011571113.

* cited by examiner

SYSTEM AND METHOD FOR MEASURING LIFE PARAMETERS DURING SLEEP

TECHNICAL FIELD

The present invention relates to a system and method for measuring life parameters during sleep. In particular, the present invention relates to constant monitoring and evaluating of life parameters, as well as reporting detected abnormal events.

BACKGROUND

In medicine, monitoring is the observation of a disease, condition or one or more medical parameters over time. It can be performed by continuously measuring certain parameters by using a medical monitor (for example, by continuously measuring vital signs by a bedside monitor), and/or by repeatedly performing medical tests (such as blood glucose monitoring with a glucose meter). Transmitting data from a monitor to a distant monitoring station is known as telemetry or biotelemetry (source: Wikipedia).

For a typical person, there are three key aspects of monitoring life parameters during sleep. They refer to different abnormal conditions typically found in different age groups.

The first age group are children from 0 to 8 months of age. Apnea usually occurs during sleep and is primarily a disorder of premature infants. Babies born before 34 weeks of gestation do not have a fully developed central nervous system, and they often do not have adequate control of the breathing reflex.

The second group of interest are children from 6 months to 3 years of age. In this age range the key monitored parameter is body temperature. Children often suffer from rapidly developing infections with very high fever. Thus, it is crucial to monitor their life parameters.

The last target group are adults suffering from obstructive sleep apnea (OSA). OSA is the most common category of sleep-disordered breathing. The muscle tone of the body ordinarily relaxes during sleep, and at the level of the throat the human airway is composed of collapsible walls of soft tissue which can obstruct breathing during sleep. Mild occasional sleep apnea, such as many people experience during an upper respiratory infection, may not be important, but chronic severe obstructive sleep apnea requires treatment to prevent low blood oxygen (hypoxemia), sleep deprivation, and other complications (source: Wikipedia).

In case of adults, heart rate may also be measured as an additional life parameter to the aforementioned.

A U.S. Pat. No. 6,062,216 discloses an apnea monitor and system for treatment includes a detector in a fixed console that projects a detection beam at a sleep surface. The detection beam is reflected off a patient on the surface and return light is analyzed to develop a signal which varies with external motion of the patient's upper body. The motion signals are then fed to a pattern recognizer which identifies breath signals and analyzes them to detect cessation or excessive pauses in breathing, and trigger an alarm or intervention to restore breathing regularity. The monitor includes a laser for generating radiation. The radiation is reflected from the patient and is directed onto a detector. The detector produces output signals corresponding to the impinging reflected light, which are processed by a control element to determine the change of movement, e.g., the breathing rate, of the patient. This method has a disadvantage of monitoring a patient externally. Thus, in case a patient changes positions during sleep or is covered with a thick quilt, the method is not reliable.

A US patent application US20030055348 discloses a method of determining a diagnostic measure of sleep apnea including the following steps: acquiring an electrocardiogram signal, calculating a set of RR intervals and electrocardiogram-derived respiratory signal from said electrocardiogram, and hence calculating a set of spectral and time-domain measurements over time periods including power spectral density, mean, and standard deviation. These measurements are processed by a classifier model which has been trained on a pre-existing data base of electrocardiogram signals to provide a probability of a specific time period containing apneic episodes or otherwise. These probabilities can be combined to form an overall diagnostic measure. The system also provides a system and apparatus for providing a diagnostic measure of sleep apnea. A disadvantage of this method is a complex equipment that may be inconvenient for a patient during sleep.

It would be advantageous to provide a compact device with improved sleep apnea and temperature detection as well as evaluation.

SUMMARY

There is disclosed a method for measuring life parameters during sleep by a device comprising an accelerometer attached to the body of a sleeping subject, the method comprising the steps of: (a) setting a hysteresis width having a maximum hysteresis value and a minimum hysteresis value; (b) reading, from the accelerometer, values of acceleration in three axes; (c) filtering the values of acceleration in each of the three axes with a band-pass filter to obtain filtered acceleration signals; (d) combining the filtered acceleration signals from each of the three axes to obtain a signal level; (e) checking whether the signal level is higher than the current maximum hysteresis value and if so, setting the maximum hysteresis value to the signal level and setting the minimum hysteresis value to the maximum hysteresis value decreased by the hysteresis width; and (f) signaling a breath detection when a transition from a falling edge to a rising edge is detected on the signal level (605, 606).

The method may comprise reading the values of acceleration in the three axes with a frequency of at least 50 Hz.

When the signal level is lower than or equal the current maximum hysteresis value, the method may comprise: checking whether the signal level is lower than the current maximum hysteresis value and if so, setting the minimum hysteresis value to the signal level and setting the maximum hysteresis value to the minimum hysteresis value increased by the hysteresis width; and detecting a transition from a rising edge to a falling edge on the signal level and setting a flag indicating such detection.

The pass band of the band-pass filter can be from 0.2 Hz to 1.1 Hz.

The filtering can be effected by applying moving average filters.

The first moving average filter may use at least 16 samples while the second moving average filter uses at least 16 latest results of the first filter over the successive sets of at least 16 samples.

Combining the filtered acceleration signals from each of the three axes may comprise calculating a sum of absolute values of the filtered acceleration signals in each of the three axes.

The method may further comprise returning to step (b) after step (f) to repeat the method steps for at least one subsequent data sample.

There is also disclosed a computer program comprising program code means for performing all the steps of the computer-implemented method as described above when said program is run on a computer, or a computer readable medium storing computer-executable instructions performing all the steps of the computer-implemented method as described above when executed on a computer, or a non-transitory computer-readable medium storing computer-executable instructions performing all the steps of the method as described above when executed on a computer.

Furthermore, there is disclosed a system for measuring life parameters during sleep, the system comprising: a data bus communicatively coupled to a memory; an accelerometer coupled to the data bus; and a controller configured to execute all the steps of the method as described above.

BRIEF DESCRIPTION OF THE DRAWINGS

These and other objects of the invention presented herein, are accomplished by providing a system and method for measuring life parameters during sleep. Further details and features of the present invention, its nature and various advantages will become more apparent from the following detailed description of the preferred embodiments shown in a drawing, in which.

NOTATION AND NOMENCLATURE

Some portions of the detailed description which follows are presented in terms of data processing procedures, steps or other symbolic representations of operations on data bits that can be performed on computer memory. Therefore, a computer executes such logical steps thus requiring physical manipulations of physical quantities.

Usually these quantities take the form of electrical or magnetic signals capable of being stored, transferred, combined, compared, and otherwise manipulated in a computer system. For reasons of common usage, these signals are referred to as bits, packets, messages, values, elements, symbols, characters, terms, numbers, or the like.

Additionally, all of these and similar terms are to be associated with the appropriate physical quantities and are merely convenient labels applied to these quantities. Terms such as "processing" or "creating" or "transferring" or "executing" or "determining" or "detecting" or "obtaining" or "selecting" or "calculating" or "generating" or the like, refer to the action and processes of a computer system that manipulates and transforms data represented as physical (electronic) quantities within the computer's registers and memories into other data similarly represented as physical quantities within the memories or registers or other such information storage.

A computer-readable (storage) medium, such as referred to herein, typically may be non-transitory and/or comprise a non-transitory device. In this context, a non-transitory storage medium may include a device that may be tangible, meaning that the device has a concrete physical form, although the device may change its physical state. Thus, for example, non-transitory refers to a device remaining tangible despite a change in state.

As utilized herein, the term "example" means serving as a non-limiting example, instance, or illustration. As utilized herein, the terms "for example" and "e.g." introduce a list of one or more non-limiting examples, instances, or illustrations.

DETAILED DESCRIPTION

Figure 1:
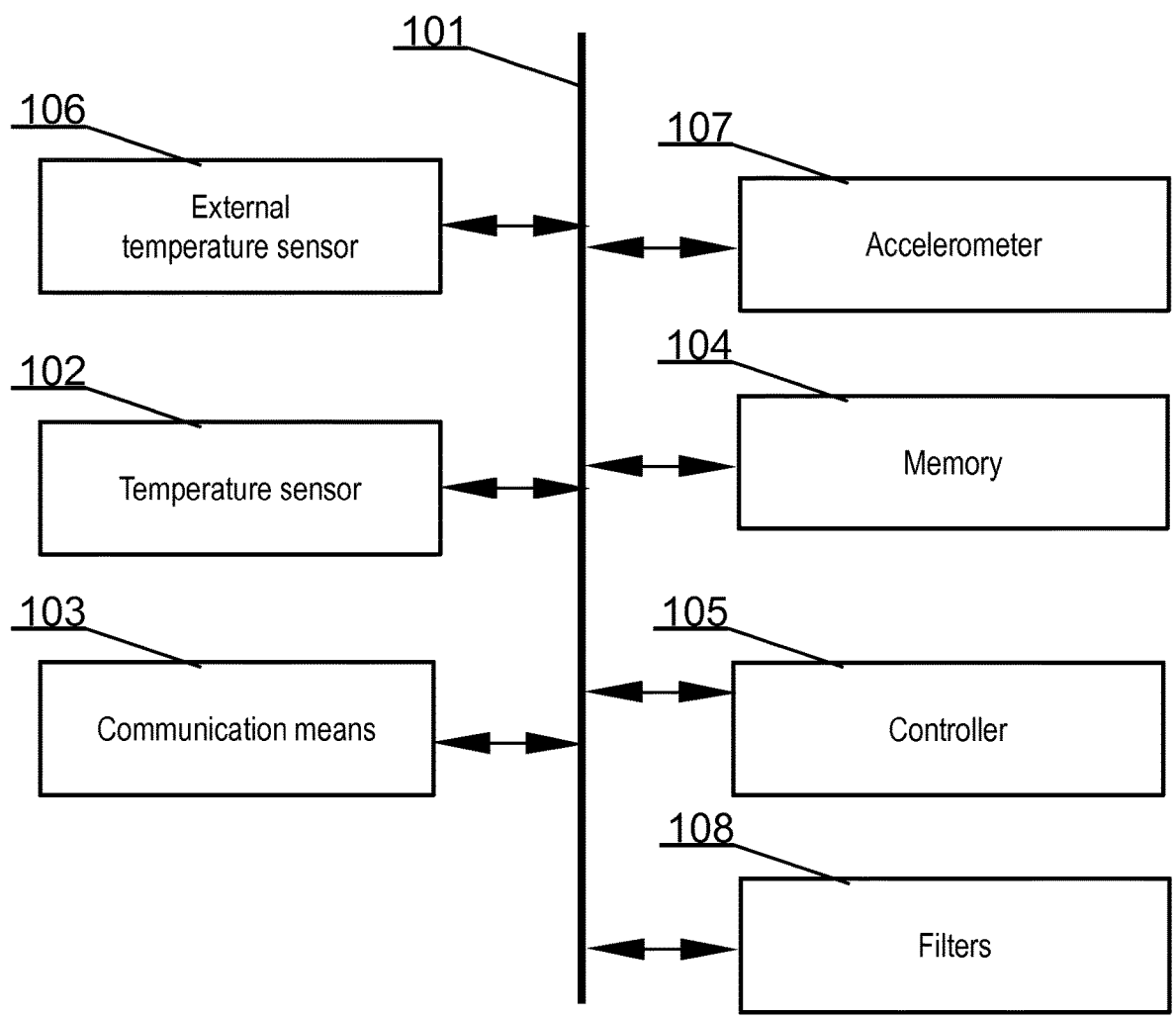
FIG. 1 presents a diagram of the system according to the present invention.

FIG. 1 presents a diagram of the system according to the present invention. The system is a temperature and breathing measuring device. Additionally, pulse may be measured, by detecting micro moves, and body moves may be monitored in order to detect sleep phases.

The system may be realized using dedicated components or custom made FPGA (Field-Programmable Gate Array) or ASIC (Application Specific Integrated Circuit) circuits. The system comprises a data bus 101 (e.g. I2C or similar) communicatively coupled to a memory 104. Additionally, other components of the system are communicatively coupled to the system bus 101 so that they may be managed by a controller 105.

The memory 104 may store computer program or programs executed by the controller 106 in order to execute steps of the method according to the present invention. Further, the memory 104 may store any temporary and final data produced by the controller.

The controller 105 may process the received data or may pass raw data to an external processing unit, preferably via a communication means 103 that may be wired or wireless (e.g. BLUETOOTH). Alternatively, the controller 105 may process the received data and transmit externally only signals on abnormal conditions, for example to a mobile phone.

The system may have several versions differing by the number and envisaged placement of temperature sensor(s). The division results from assumed ages of monitored persons as well as from the characteristics of the measured parameters. For example, it is best to measure temperature in an armpit while breathing is best measured at abdomen.

In a first embodiment, the system may comprise an external temperature sensor 106, preferably for positioning in an armpit.

In a second embodiment, the system may comprise at least one temperature sensor 102, preferably at the exterior of its casing, wherein a temperature sensor may measure ambient temperature or body temperature.

The temperature sensor may be TMP112AIDRLT offered by TEXAS INSTRUMENTS. It is sufficiently precise, has 12-bit processing and digital communication capabilities.

Additionally, the present system comprises an accelerometer 107. An accelerometer is a device that measures proper acceleration ("g-force"). Proper acceleration is not the same as coordinate acceleration (rate of change of velocity). For example, an accelerometer at rest on the surface of the Earth will measure an acceleration g=9.81 m/s^2 straight upwards. By contrast, accelerometers in free fall (falling toward the center of the Earth at a rate of about 9.81 m/s^2) will measure zero.

Accelerometers have multiple applications in industry and science. Highly sensitive accelerometers are components of inertial navigation systems.

The controller 105 requests data from the accelerometer 107 and the temperature sensor(s). Then the data is processed and the results are stored. In case of detection of an abnormal condition, the controller 107 may be configured to signal an event that may be indicated by the system e.g. by a sound or a light indication, or be transmitted to an external device.

Lastly, the present system comprises a filters module 108 required for filtering of the accelerometer data. Details of such filtering have been presented with reference to FIG. 2.

Figure 2:
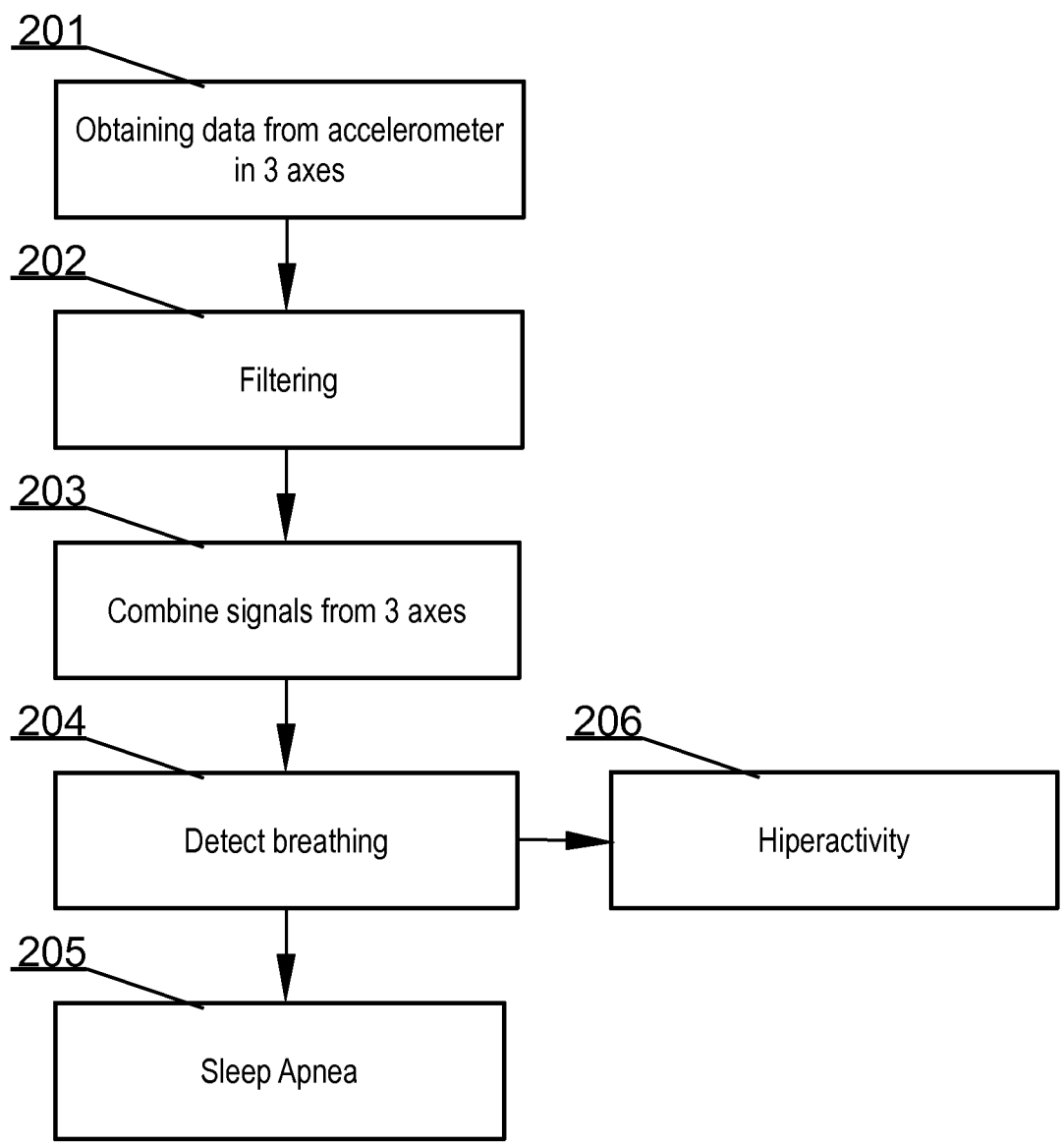
FIG. 2 presents a diagram of the method according to the present invention.
Figure 4:
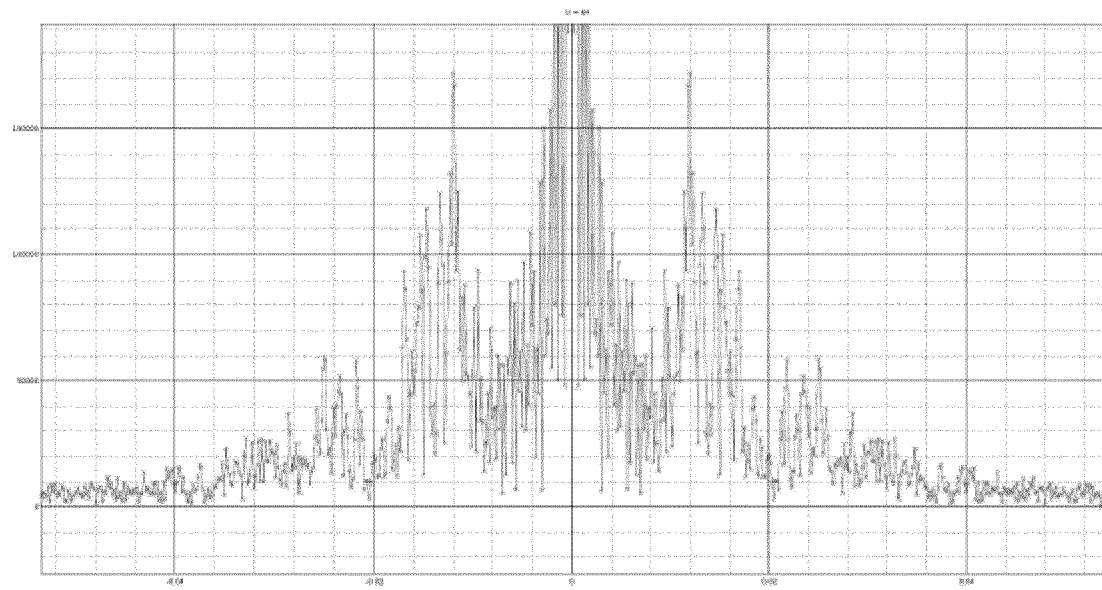
FIG. 4 shows a signal waveform of breathing of a several-months-old child.

FIG. 2 presents a diagram of the method according to the present invention. The method starts at step 201 from acquiring samples of data from the accelerometer 107. Samples may be gathered over a period of time in order to obtain a signal variable in time. FIG. 4 shows a signal waveform of breathing of a several-months-old child as sampled.

Preferably, the controller 105 reads data from the accelerometer 107 with a frequency of at least 50 Hz (i.e. it reads data every 20 ms or more frequently) by using the data bus 101. These data denote acceleration values in all three accelerometer axes. Naturally, other sampling frequencies may be applied.

Analysis of the sampled signal is executed by using a method of detection of a maximum and minimum value with a moving hysteresis (time-based dependence of a system's output on present and past inputs).

Regarding the aforementioned maximum and minimum values, the present method applies a joint movement, of both the maximum and the minimum level of the hysteresis window (i.e. the maximum hysteresis and the minimum hysteresis parameters appropriately). This means that the width of the hysteresis is constant (i.e. the difference between the maximum hysteresis and the minimum hysteresis parameters is constant) but rather its placement on the Y axis changes.

The width of the hysteresis is system-specific and selected experimentally depending on e.g. the desired sensitivity of the system.

Increasing values received by the method, result in, after crossing a maximum hysteresis level, moving the hysteresis towards higher values. The maximum hysteresis value is at this point determined as the signal level while the minimum hysteresis value equals a difference between the signal level and a predefined hysteresis width.

The hysteresis width may be adapted to measurement conditions and is aimed at reducing interferences of noise. In particular, it is the aim of setting up the hysteresis width so that noise present, which does not exceed the hysteresis width, will not affect breathing detections.

A change of signal level monotonicity for example from a rising to a different monotonicity, will not immediately result in for example moving the hysteresis downwards on the Y axis. This will happen when the signal level crosses the current minimum hysteresis value. At this moment the minimum hysteresis value will be determined at the signal level while the maximum hysteresis value will be determined at the level equaling a sum of the signal level (filtered and combined data from accelerometer in 3 axes) and a predefined hysteresis width. A movement of the hysteresis towards the rising value followed by a movement towards the falling values will denote a breath.

Thus, the minimum and the maximum amplitude values are obtained after merging signals from the three accelerometer axes. Further, in case breathing is not detected i.e. accelerometer's signal amplitude is lower than a value of the hysteresis, a timer may be started. When the time without breath reaches a predefined threshold, for example 15 seconds, an abnormal event may be signaled.

The method detects a rising edge or a falling edge of the signal and appropriately corrects the hysteresis value as defined above.

A change of a monitored edge is present when the signal crosses hysteresis value appropriately separated (by a predefined threshold) from a previously stored minimum or maximum value.

For example, for a rising edge, a maximum value is constantly updated as well as the lower level of the hysteresis, which is a difference between the maximum value and the hysteresis width.

This is effected until the signal reaches a peak value and starts to fall. The lower level of hysteresis value will start to monitor the signal by appropriately decreasing the upper hysteresis value.

This approach does not report false positive results when significant surging is present e.g. due to movement of a monitored person.

This method has been selected based on a series of trials and results in nearly 100% correct detections of breathing patterns.

Figure 5:
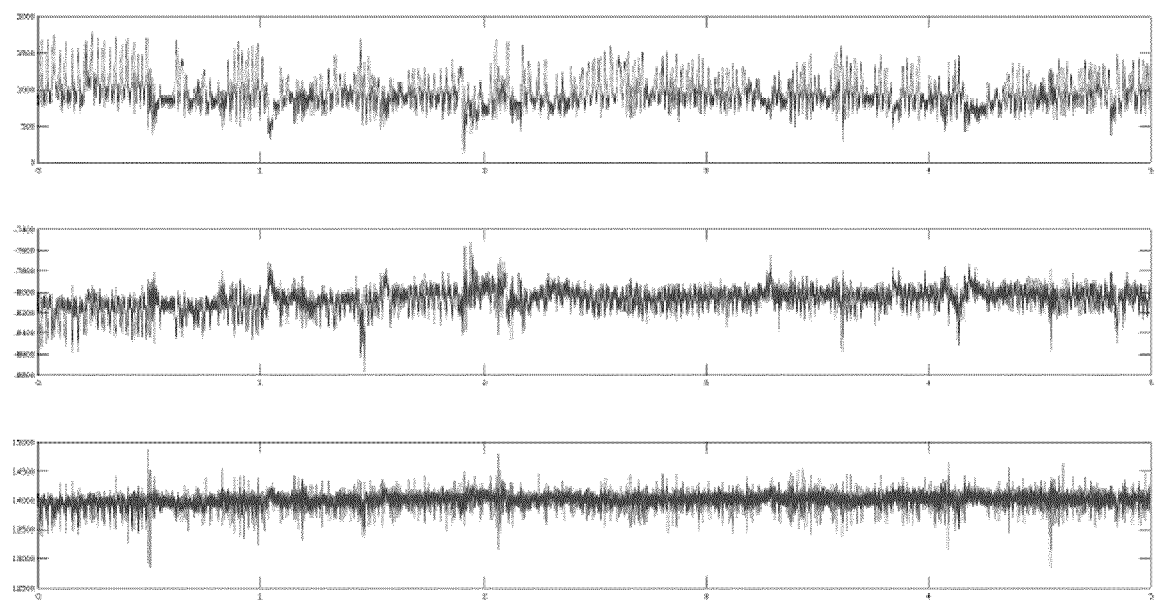
FIG. 5 presents a signal comprising the strong constant component.

The next step of the method 202, is a low-pass and high-pass filtering of the signal. The signal comprises a strong constant (DC) component, which is a result of earth's gravity. Since the device should detect small differences in signals this strong constant component should be filtered. FIG. 5 presents a signal comprising the strong constant component.

After the strong constant component the highest concentration of components is present at discrete frequencies around 0.012, which translates to a real frequency of 0.6 Hz (the sampling frequency has been set at 50 Hz).

Research shows that breathing frequency of children of the age up to 3 years is within a range of between 0.3 Hz and 1 Hz. Thus frequencies above 1 Hz may be discarded as noise and interferences (e.g. heart motion).

Thus, the cut off frequencies of the band-pass filter are preferably set at from 0.2 Hz to 1.1 Hz. A band-pass filter may be configured as a difference between two low-pass filters.

Further, moving average filters have been applied: a first filtered averaging 16 samples and a second filter averaging the square number of samples of the first filter, i.e. 256 samples. Filters averaging more samples can be used as well.

The filter is a band-pass filter implemented as a difference of two moving averages having a different time window. The first moving average is used as a low-pass filter and is calculated over the latest 16 samples. The second moving average is calculated over 16 latest results of the first moving average (over successive sets of 16 samples), which after a subtraction serves as a high-pass filter. The operation of the filter results in decrease of influence of high frequency interferences and removal of a constant component from the signal as well as low frequencies.

The filtering is executed for signals from each axis wherein these signals are combined i.e. there is defined a sum of absolute values. From this moment onwards, these are the values used to calculate a hysteresis.

Figure 3:
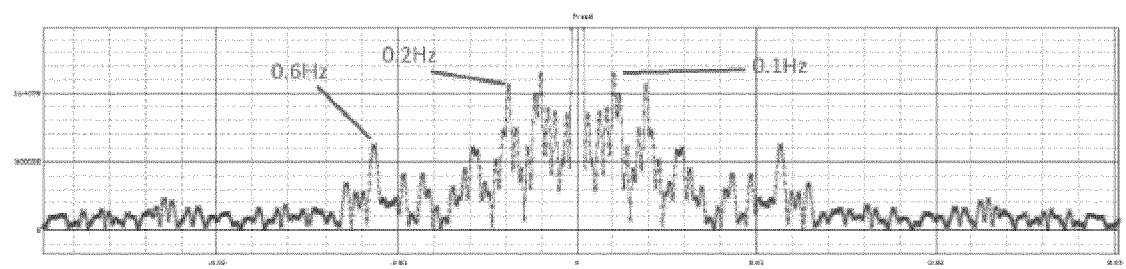
FIG. 3 presents a raw and filtered signal comparison.
Figure 3:
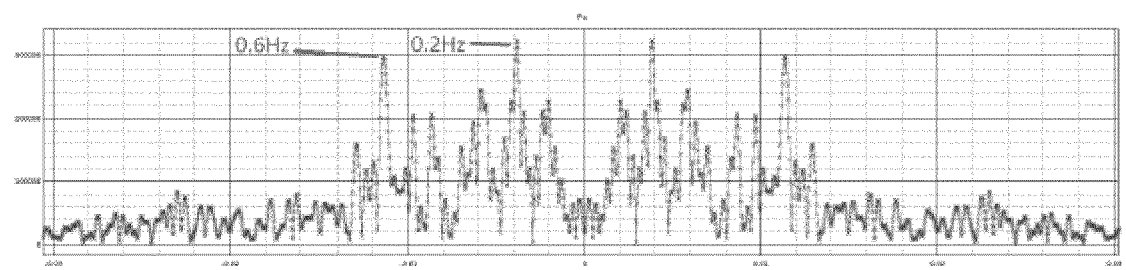

FIG. 3 presents a raw and filtered signal comparison. As may be seen, after filtration, spectral lines 0.2 Hz and 0.6 Hz are more clear, while the strong constant component has been removed.

After filtering in step 202 the signals of 3 axes are combined (a sum of absolute values) in step 203. Subsequently, at step 204 breathing is detected by finding local peaks in a signal waveform (minimums and maximums) with an application of an appropriate hysteresis, which allows for further filtering of interferences.

In case the method does not detect any acceleration condition, caused by chest movements, within e.g. 15 seconds, it signals an alarm event in step 205. Otherwise, if movements detected are too frequent (e.g. above 6 Hz), there may be signaled an alarm event on hyperactivity 206.

Figure 6:
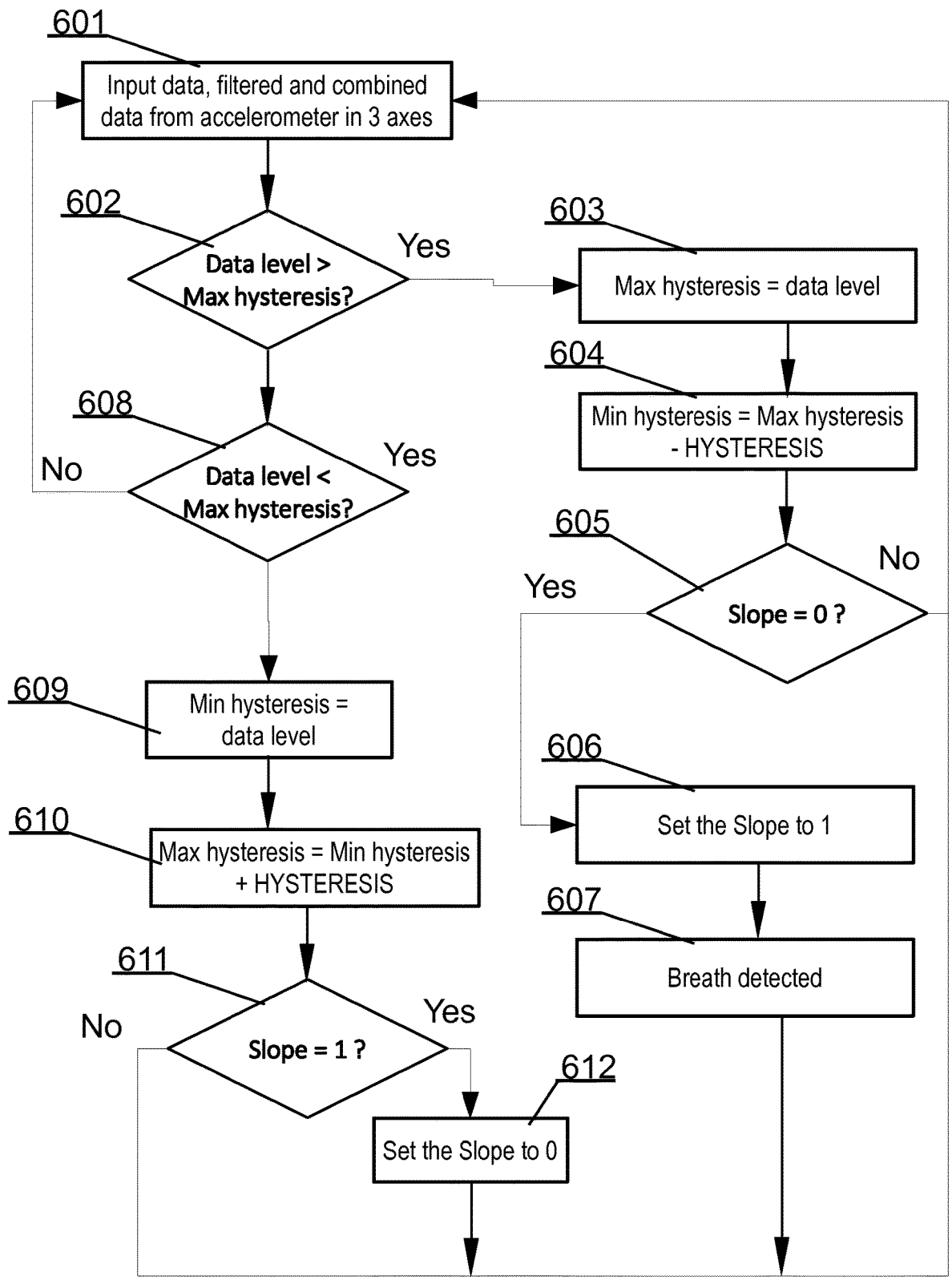
FIG. 6 presents signal monitoring and hysteresis modification (movement).

FIG. 6 presents signal monitoring and hysteresis modification (movement). At step 601 the method reads signal level i.e. filtered and combined data from accelerometer in 3 axes as previously described with respect to the two moving averages having a different time window. The Slope parameter value is initialized to 0 and a predefined hysteresis width (HYSTERESIS) is set up using the minimum and maximum hysteresis values.

Subsequently, at step 602, it is checked whether signal level is higher than the current maximum hysteresis value. In case it is (denoting a rising edge of the signal), the method proceeds to step 603 where the maximum hysteresis value is set to the signal level.

Subsequently, at step 604, the minimum hysteresis value is set to the maximum hysteresis value decreased by the predefined hysteresis width. Next, at step 605, it is checked whether a falling edge of the signal level has previously occurred (0 denotes that the signal level has been falling while a 1 denotes that signal level has been rising) and if it has, a flag (Slope) signaling the signal level edge is set to 1 in step 606 and breath detection is signaled in step 607. In other words, a breath detection is signaled when a transition from a falling edge to a rising edge is detected on the signal level.

Otherwise, when at step 602 signal level is higher than the current maximum hysteresis value, the method proceeds to step 608 where it is checked whether signal level is lower than the current maximum hysteresis value. In case it is (denoting a falling edge of the signal), the method proceeds to step 609 where the minimum hysteresis value is set to the signal level. Subsequently, at step 610, the maximum hysteresis value is set to the minimum hysteresis value increased by the predefined hysteresis width.

Next, at step 611, it is checked whether a rising edge of the signal level has previously occurred (1 denotes that the signal level has been rising while a 0 denotes that signal level has been falling) and if it has, a flag (Slope) signaling the signal level edge is set to 0 in step 612. In other words, a transition from a rising edge to a falling edge is detected on the signal level.

The aforementioned approach has an advantage that even if it there is noise present, which does not exceed the hysteresis width, the detection will not be impaired and the hysteresis will move accordingly until a rising edge is detected.

The aforementioned invention results in detection of sleep apnea condition and thus serves as a human being life parameters monitoring tool that may detect serious conditions. Therefore, the invention provides a useful, concrete and tangible result.

According to the present invention, data from an accelerometer are sampled, by a specially configured processing system, and processed in order to detect proper or abnormal breathing condition. Therefore, the machine or transformation test is fulfilled and that the idea is not abstract.

At least parts of the methods according to the invention may be computer implemented. Accordingly, the present invention may take the form of an entirely hardware embodiment, an entirely software embodiment (including firmware, resident software, micro-code, etc.) or an embodiment combining software and hardware aspects that may all generally be referred to herein as a "circuit", "module" or "system".

Furthermore, the present invention may take the form of a computer program product embodied in any tangible medium of expression having computer usable program code embodied in the medium.

It can be easily recognized, by one skilled in the art, that the aforementioned method for measuring life parameters during sleep may be performed and/or controlled by one or more computer programs. Such computer programs are typically executed by utilizing the computing resources in a computing device. Applications are stored on a non-transitory medium. An example of a non-transitory medium is a non-volatile memory, for example a flash memory while an example of a volatile memory is RAM. The computer instructions are executed by a processor. These memories are exemplary recording media for storing computer programs comprising computer-executable instructions performing all the steps of the computer-implemented method according the technical concept presented herein.

While the invention presented herein has been depicted, described, and has been defined with reference to particular preferred embodiments, such references and examples of implementation in the foregoing specification do not imply any limitation on the invention. It will, however, be evident that various modifications and changes may be made thereto without departing from the broader scope of the technical concept. The presented preferred embodiments are exemplary only, and are not exhaustive of the scope of the technical concept presented herein.

Accordingly, the scope of protection is not limited to the preferred embodiments described in the specification, but is only limited by the claims that follow.

The invention claimed is:

1. A method for measuring life parameters during sleep comprising steps of:
setting a maximum hysteresis value, a minimum hysteresis value and a hysteresis width which is the maximum hysteresis value minus the minimum hysteresis value;
reading, from an accelerometer, values of acceleration along three orthogonal axes, the accelerometer being attached to a body of a sleeping subject;
filtering the values of acceleration in each of the three orthogonal axes with a band-pass filter to obtain filtered acceleration signals;
combining the filtered acceleration signals from each of the three orthogonal axes to obtain a signal level;
determining that the signal level is higher than the maximum hysteresis value;
setting the maximum hysteresis value to a new maximum hysteresis value that is the signal level and setting the minimum hysteresis value to the new maximum hysteresis value minus the hysteresis width; and
signaling a breath detection when the signal level is detected to transition from falling to raising.

2. The method according to claim 1, wherein the reading of the values of acceleration occurs at a frequency of at least 50 Hz.

3. The method according to claim 1, wherein the pass band of the band-pass filter is from 0.2 Hz to 1.1 Hz.

4. The method according to claim 1, wherein the filtering is effected by applying moving average filters.

5. The method according to claim 4, wherein a first moving average filter of the moving average filters uses at least 16 samples while a second moving average filter of the moving average filters uses at least 16 latest results of a first filter over successive sets of at least 16 samples.

6. The method according to claim 1, wherein combining the filtered acceleration signals from each of the three orthogonal axes comprises calculating a sum of absolute values of the filtered acceleration signals in each of the three orthogonal axes.

7. The method according to claim 1, further comprising providing an alarm if the breath detection is not signaled for a predetermined amount of time.

8. The method according to claim 7, wherein the predetermined amount of time is 15 seconds and the alarm is at least one of a sound or light indication.

9. The method according to claim 1, wherein all of the steps are performed by a computer executing computer-executable instructions stored on a non-transitory computer readable medium.

10. A non-transitory computer-readable medium storing computer-executable instructions, when executed on a computer, performing:
   setting a maximum hysteresis value, a minimum hysteresis value and a hysteresis width which is the maximum hysteresis value minus the minimum hysteresis value;
   reading, from an accelerometer, values of acceleration along three orthogonal axes, the accelerometer being attached to a body of a sleeping subject;
   filtering the values of acceleration in each of the three orthogonal axes with a band-pass filter to obtain filtered acceleration signals;
   combining the filtered acceleration signals from each of the three orthogonal axes to obtain a signal level;
   determining that the signal level is higher than the maximum hysteresis value;
   setting the maximum hysteresis value to a new maximum hysteresis value that is the signal level and setting the minimum hysteresis value to the new maximum hysteresis value minus the hysteresis width; and
   signaling a breath detection when the signal level is detected to transition from falling to raising.

11. A system for measuring life parameters during sleep, the system comprising:
   a memory;
   a data bus communicatively coupled to the memory;
   an accelerometer coupled to the data bus the accelerometer being configured to be attached to a body of a sleeping subject;
   a band-pass filter; and
   a controller configured to:
   set a maximum hysteresis value, a minimum hysteresis value and a hysteresis width which is the maximum hysteresis value minus the minimum hysteresis value;
   communicate with the accelerometer to obtain values of acceleration along three orthogonal axes;
   filter the values of acceleration in each of the three orthogonal axes with the band-pass filter to obtain filtered acceleration signals;
   combine the filtered acceleration signals from each of the three orthogonal axes to obtain a signal level;
   determine whether the signal level is higher than the maximum hysteresis value;
   when the signal level is determined to be higher than the maximum hysteresis value, set the maximum hysteresis value to a new maximum hysteresis value that is the signal level and setting the minimum hysteresis value to the new maximum hysteresis value minus the hysteresis width; and
   signal a breath detection when the signal level is detected to transition from falling to raising.

12. The system according to claim 11, further comprising an alarm that provides an indication when a predetermined period of time elapses without the breath detection.

13. The system according to claim 12, wherein the alarm is further configured to provide an indication of hyperactivity.

14. The system according to claim 11, wherein the band-pass filter is configured as a difference between two low-pass filters.

15. The system according to claim 11, wherein the band-pass filter is configured as a difference of two moving averages having a different time window.

* * * * *